US006852338B2

(12) United States Patent
Oakes

(10) Patent No.: US 6,852,338 B2
(45) Date of Patent: Feb. 8, 2005

(54) NON-LETHAL METHOD FOR EXTRACTING CRUDE HEMOCYANIN FROM GASTROPOD MOLLUSCS

(75) Inventor: Frank R. Oakes, Port Hueneme, CA (US)

(73) Assignee: Stellar Biotech, Inc., Port Hueneme, CA (US)

( * ) Notice: Subject to any disclaimer, the term of this patent is extended or adjusted under 35 U.S.C. 154(b) by 377 days.

(21) Appl. No.: 10/124,708

(22) Filed: Apr. 18, 2002

(65) Prior Publication Data
US 2002/0192633 A1 Dec. 19, 2002

Related U.S. Application Data
(60) Provisional application No. 60/284,979, filed on Apr. 18, 2001.

(51) Int. Cl.$^7$ ............................................... A61K 35/56
(52) U.S. Cl. ..................................................... 424/547
(58) Field of Search ................................. 424/537, 547

(56) References Cited

U.S. PATENT DOCUMENTS 6,054,317 A 4/2000 McMahon
6,326,485 B1 12/2001 Vasta et al.

OTHER PUBLICATIONS

Gauthier et al., Journal of Shellfish Research 9(2): 367–371 (1990).*
Rees et al., Llmnology and Oceanography 38(1): 213–217 (1993).*
Chen, Acta Zoologica Taiwanica 7(1): 61–71 (1996).*
J.F. Illingworth, "The Anatomy of *Lucapina crenulata* Gray" 449–480.
Prakash Dube, et al, "Three–Dimensional Structure of Keyhole Limpet Hemocyanin by Cryoelectron Microscopy and Angular Reconstitution", Journal of Structural Biology 115, 226–232 (1995).
Wolfgang Gebauer, et al, "Controlled cleavage of KLH1 and KLH2 by the VB protease from *Staphylococcus aureus*—Reassociation, electrophoretic and transmission electron microscopy study of peptide fragments", Eur. J. Biochem 262, 166–175 (1999).
Wolfgang Gebauer, et al, "Quatemary structure, subunits and domain patterns of two discrete forms of keyhole limpet hemocyanin: KLH1 and KLH2", Zoology—Analysis of Complex Systems, vol. 98, No. 1, (1994).
J. Robin Harris, et al., "Electron microscopy of a double helical tubular filament in keyhold limpet (*Megathura crenula*) hemolymph", Cell & Tissue Research, 411–420 (1992).
J. Robin Harris, et al., "Electron microscopy and biochemical characterization of a 350–kDa annular hemolymph protein from the keyhole limpet *Megathura crenulate*", Eur. J. Biochem, 225, 521–528 (1994).
J. Robin Harris, et al., "Keyhold Limpet Hemocyanin (KLH), II: Characteristic Reassociation Properties of Purified KLH1 and KLH2", Micron, vol. 28, No. 1, pp. 43–56 (1997).
J.R. Harris, et al., "Keyhole limpet hemocyanin (KLH): a biomedical review", Micron 30 (1997) 597–623.

(List continued on next page.)

Primary Examiner—Jean C. Witz
(74) Attorney, Agent, or Firm—Foley & Lardner LLP

(57) ABSTRACT

The present invention is directed to methods for collecting a commercially useful quantity of crude hemocyanin from live gastropod molluscs by isolating hemolymph in a sinus of the animal followed by extraction of the hemolymph. The methods of the invention do not require incision of the vascular system or injury or death to the animal. In addition, the methods of the invention enable the periodic extraction of hemolymph from the same source animals.

27 Claims, 2 Drawing Sheets

OTHER PUBLICATIONS

N.M. Senozan, et al., "Hemocyanin of the Giant Keyhole Limpet, *Megathura crenulata*" 703–717.

Richard D. Swerdlow, et al., "Keyhole Limpet Hemocyanin: Structural and Functional Characterization of Two Different Subunits and Multimers", Biochem. Physiol. vol. 113B, No. 3, pp. 537–548 (1996).

Arthur A. Vandenbark, et al., "All KLH Preparations Are Not Created Equal", Cellular Immunology 60, 240–243 (1981).

Chen, "Hemolymph Collection in Abalone (Haliotis Diversicolor)", *Acta Zoologica Taiwanica*, vol. 7, No. 1, 1996, pp. 61–71, XP002275452, ISSN: 1019–5858.

Yanick et al., "Survival and Growth of Mussels Subsequent to Hemolymph Sampling for DNA", *Journal of Shellfish Research*, vol. 19, No. 2, Dec. 2000 (Dec. 2001), pp. 991–993, XP002275453, ISSN: 0730–8000.

\* cited by examiner

NON-LETHAL METHOD FOR EXTRACTING CRUDE HEMOCYANIN FROM GASTROPOD MOLLUSCS

SUMMARY OF THE INVENTION

The present invention is directed to methods of collecting hemolymph from gastropod molluscs. The method does not require sacrificing the mollusc, as the method is conducted while the mollusc is alive, without causing death or adverse long-term impacts on the health of the animal.

BACKGROUND OF THE INVENTION

For decades it has been known that hemocyanins are among the most potent of immunogens. Hemocyanins, including Keyhole Limpet Hemocyanin (KLH; from the Prosobranch Gastropod Mollusc *Megathura crenulata*) have been widely used and extensively studied. See Haris et al., "Keyhole limpet hemocyanin (KLH): a Biomedical Review," *Micron*, 30(6):597–623 (1999). The high antigenicity of purified hemocyanins, coupled with the relative ease of covalent conjugation with other antigens, has historically made KLH and other hemocyanins a common and familiar tool for establishing baseline immune responses in clinical research and as immunogenic carriers of many haptens in biomedical research.

Uses for hemocyanins have recently expanded, as they are now being tested as therapeutic agents and adjuvants. For example, as an active biotherapeutic agent the hemocyanin KLH is currently being tested clinically in the treatment of certain cancers, including superficial transitional cell carcinoma of the bladder (TCC) (Haris et al. (1999), and Swerdlow et al., "Keyhole Limpet Hemocyanin: Structural and Functional Characterization of Two Different Subunits and Multimers," *Comparative Biochem. & Physiology, Part B, Biochem. & Mol. Biol.*, 113(3):537–48 (March 1998)), metastasis breast cancer (Biomira, Inc. Company Press Release, Biomira.com, 2001), malignant melanoma, and also as an immune response assay in AIDS research (Kahn et al., "A Phase I study of HGP-30, An Amino Synthetic Peptide Analog Sub-Unit Vaccine in Seronegative Subjects," *AIDS Res. Hum. Retrovirus*, 8:1321–1325 (1992); and WO 90/03984 for "Human Immunodeficiency Virus (HIV) Proteins and Peptides Containing the Principal Neutralizing Domain and Their Use in Diagnosis, Prophylaxis, or Therapy of AIDS"). Moreover, hemocyancins are a promising tumor vaccine carrier. See e.g., Thurnher et al., "Dendric Cell-Based Immunotherapy on Renal Cell Carcinoma," *Urol. Int.*, 61:67–71 (1998); Slovin et al., "Peptide and Carboyhydrate Vaccines in Relapsed Prostrate Cancer: Immunogenicity of Synthetic Vaccines in Man," *Cancer Center Sernin Oncol.*, 26:448–454 (1999); Massaia et al., "Idiotype Vaccination in Human Melanoma: Generation of Tumor-Specific Immune Responses After High-Dose Chemotherapy," *Blood*, 94:673–683 (1999); Fujii et al., "Presentation of Tumor Antigens by Phagocytic Dendritic Cell Clusters Generated From Human CD34+ Hemotopoietic Progenitor Cells: Induction of Autologous Cytotoxic T Lymphocytes Against Leukemic Cells in Acute Myloge-neous Leukemia Patients," *Cancer Res.*, 59:2150–2158 (1999); Ragupathi et al., "Vaccines Prepared With Sialyl-Tn and Sialyl-Tn Trimers Using 4-(4-maleimidomethyl) Cyclohexane-1-Carboxyl Hydratide Linker Group Result in Optimal Antibody Titers Against Ovine Submaxillary Mucin and Sialyl-Tn-Positive Tumor Cells," *Cancer Immunol. Immunother.*, 48:1–8 (1999); Sloven et al., "Carbohydrate Vaccines in Cancer: Immunogenicity of a Fully Synthetic Globo H Hexasaccharide Conjugate in Man," *PNAS, USA*, 96:5710–5715 (1999); Hsu et al., "Tumor-Specific Idiotype Vaccines in the Treatment of Patients with B-Cell Lymphoma—Long Term Results of a Clinical Trial," *Blood*, 89:3129–3135 (1999); Dickler et al., "Immunogenicity of a Fucosyl-GM1-Keyhole Limpet Hemocyanin Conjugate Vaccine in Patients with Small Cell Lung Cancer," *Clin. Cancer Res.*, 5:2773–2779 (1999); Adluri et al., "Specific Analysis of Sera From Breast Cancer Patients Vaccinated with MUC1-KLH Plus QS-21," *Br. J. Cancer*, 79:1806–1812 (1999); and Sandmaier et al., "Evidence of a Cellular Immune Response Against Sialyl-Tn in Breast and Ovarian Cancer Patients After High Dose Chemotherapy, Stem Cell Rescue, and Immunization with Theratope STn-KLH Cancer Vaccine," *J. Immunotherapy*, 22:55–66 (1999).

Structure of Gastropod Hemocyanins

To date, isolation of hemocyanins from animals is the only source of these proteins, as efforts to recombinantly produce the proteins have not yet succeeded. Hemocyanins are complex proteins. The most complex mulluscan hemocyanin version is found in gastropods. Biologically, hemocyanins from gastropod molluscs (such as KLH and the hemocyanin from *Haliiotis tuberculata*, HTH) are blue copper proteins which serve as oxygen carriers in the blood of the animal. The gastropod protein is a hollow cylinder of about 35 nm in diameter with an intricate internal structure. This cylinder is a didecamer based on a 400 kDa polypeptide (the subunit) which forms, in an anti-parallel manner, a stable homo-dimer. Five such homo-dimers constitute the basic cylinder (the decamer, molecular mass of about 4 Mda), which pairwise assemble face-to-face to form the quaternary structure usually found in vivo. Markl et al., *J. Cancer Res.*, 127(Suppl. 2):R3–R9 (2001). The gastropod hemocyanin subunit itself is subdivided into eight different functional units (FUs, termed FU-a to FU-h, about 50 kDa each).

Gastropod molluscan hemocyanins occur as two distinct isoforms. Each of these molecules is based on a very large polypeptide chain, the subunit which is folded into a series of eight globular functional units. Twenty copies of this subunit form a cylindrical quaternary structure. Markl et al., "Marine Tumor Vaccine Carriers: Structure of the Molluscan Hemocyanins KLH and HTH," *J. of Cancer Res.*, 127, Supplm. 2, pp. R309 (October 2001).

The first complete primary structure of a gastropod hemocyanin subunit was described in 2000. The 3404 amino acid sequence of the hemocyanin isoform HTH1 from *Haliiotis tuberculata* is the largest polypeptide sequence ever obtained for a respiratory protein. Lieb et al., "The Sequence of a Gastropod Hemocyanin (HTH1)," *J. of Bio. Chem.*, 275:5675–5681 (2000). The cDNA comprises 10,758 base pairs and includes the coding regions for a short signal peptide, the eight different functional units, a 3'-untranslated region of 478 base pairs, and a poly(A) tail. Id. Only recently were the genes coding for molluscan hemocyanins described. Lieb et al., "Structures of Two Molluscan Hemocyanin Genes: Significance for Gene Evolution," *PNAS, USA*, 98:4546–4551 (Apr. 10, 2001).

Isolation of Hemocyanin

Because hemocyanins cannot yet be made recombinantly, the proteins must be isolated from hemolymph obtained from source animals. Traditionally, hemocyanin was obtained from hemolymph from the Prosobranch Gastropod Mollusc *Megathura crenulata*. More recently, the market for gastropod hemocyanins has expanded to include hemocyanin from *Haliotis tuberculata* and *Concholepus conchole-*

*pus*. The hemolymph from other gastropod molluscs is also under investigation for useful properties.

There are a variety of well-known methods for purifying hemocyanins from crude hemolymph, which is the biological source of hemocyanins. These methods include differential centrifugation, gel-permeation chromatography, and ion-exchange chromatography. U.S. Pat. No. 5,407,912 to Ebert for "Method of Treating Bladder Cancer with a Keyhole Limpet Hemocyanin." Purified hemocyanins are commercially available in many forms.

Despite extensive literature regarding methods for purification of hemocyanins, the only methods described for collection of crude hemolymph from the Prosobranch Gastropod source animals to produce commercially valuable quantities of hemolymph require incision of the vascular system causing death of the source animal. Vanderbark et al., "All KLH Preparations Are Not Created Equal," *Cellular Immunology*, 60:240–243 (1981). Methods described for collection of hemolymph for research purposes involve inserting a needle into the muscle of the foot to penetrate the pedal blood sinus. Harris et al., "Keyhole Limpet Haemocyanin: Negative Staining in the Presence of Trehalose," *Micron*, 26(1):25–33 (1995).

Due to the anatomy of the vascular system of gastropod molluscs, the pedal sinus does not contain a significant volume of hemolymph and is not readily re-supplied with hemolymph from the heart. Additionally, insertion of a needle through the muscle of the foot results in muscular contractions that further restrict blood flow to the pedal sinus. As a result, the described methods for extraction of hemolymph either are inherently lethal, or are sufficient to only to yield minute quantities of hemolymph for research purposes.

Historically, these limitations on the supply of hemocyanins have not been significant because hemocyanins were principally used in research applications requiring only small quantities. More recently however, the incorporation of hemocyanins into promising new therapeutic products (see e.g., Jurincic-Winkler et al., "Antibody Response to Keyhole Limpet Hemocyanin (KLH) Treatment in Patients with Superficial Bladder Carcinoma," *Anticancer Res.*, 16(4A):2105–10 (1996); and Biomira, Inc. Company Press Release, Biomira.com, 2001) has resulted in the need for a sustainable supply of commercial quantities of hemocyanin produced under conditions that meet the health and safety standards imposed by the United States Food and Drug Administration and other regulatory agencies.

This need for a uniform and sustainable supply of hemocyanin produced under Good Manufacturing Procedures for pharmaceutical applications has created a need for a method to safely and repeatedly extract commercial quantities of hemocyanin from animals grown in a controlled environment. The present invention satisfies these needs.

SUMMARY OF THE INVENTION

The present invention is directed to methods of obtaining commercially useful quantities of hemolymph from gastropod molluscs. The method is conducted while the mollusc is alive, without causing death or adverse long-term impacts on the health of the animal.

The methods of the invention comprise isolating hemolymph in a region of the mollusc prior to extraction to enable a greater collection amount, and extracting only a sub-lethal quantity of hemolymph to avoid death or adverse long-term impacts on the health of the animal.

In one embodiment of the invention, a gastropod mollusc is immobilized such that gravity causes the hemolymph in the vascular system of the mollusc to flow directly from the aorta into the cephalic region of the animal, and collect in a sinus region, such as the buccal or cardiac sinus. A sub-lethal quantity of hemolymph can then be extracted from the sinus region, following which the animal can be returned to a suitable aquatic environment for recovery.

In another embodiment of the invention, centrifugation or another suitable method can be used to concentrate hemolymph in the cephalic region of the animal to enable collection from the sinus region of a sub-lethal quantity of hemolymph. After collection, the mollusc is immediately returned to a suitable aquatic environment for recovery.

Both the foregoing general description and the following brief description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

DETAILED DESCRIPTION OF THE INVENTION

The present invention is directed to methods of obtaining commercially useful quantities of hemolymph from gastropod molluscs. The method is conducted while the mollusc is alive, without causing death or adverse long-term impacts on the health of the animal.

The methods of the invention enable collection of commercially useful quantities of hemolymph from gastropod molluscs without the need to incise the vascular system or cause injury or death to the animal. In addition, the methods of the invention enable the periodic extraction of hemolymph from the same source animals. Hemolymph can be collected under sterile conditions suitable for medical and pharmaceutical uses. For example, a hollow needle can be used to extract the hemolymph from the animal and collected in an attached sterile collection device.

Furthermore, the methods of the invention allow reliance on a finite and managed population of animals to provide an indefinite and predictable supply of hemocyanin to support the development and commercialization of important hemocyanin-based therapeutic agents. Finally, the methods of the invention alleviate the need to rely on animals obtained from a dwindling and potentially threatened natural resource for the continued supply of hemocyanins.

The methods of the invention can be utilized on any suitable mollusc, such as molluscs from the genuses *Megathura, Haliotis, Concholepus*, and *Fissurella*. Exemplary useful molluscs are the Giant Keyhole Limpet *Megathura Crenulata, Haliiotis tuberculata*, and *Concholepus concholepus*.

In one method of the invention, a living gastropod mollusc is immobilized or suspended, typically head down, such that gravity causes the hemolymph in the vascular system of the mollusc to flow directly from the aorta into the cephalic region of the animal and collect in a sinus region, such as the buccal sinus 1 or cardiac blood sinus 8. The mollusc can be immobilized using any suitable means, such as a human hand or an apparatus. An exemplary apparatus is shown in FIG. 3.

Figure 1:
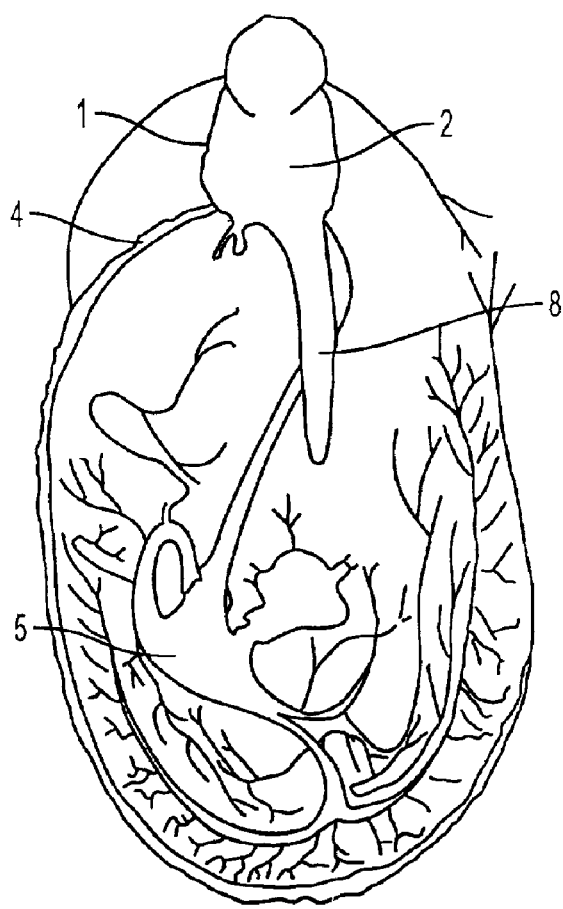
FIG. 1 shows a dorsal view of the vascular anatomy of *Megathura crenulata*, a typical Prosobranch Gastropod Mollusc, identifying the location of the buccal sinus 1, the cardiac sinus 8, the pedal artery 4, the aorta 5, and the preferred point of insertion of a hollow needle for collection of hemolymph 2.
Figure 2:
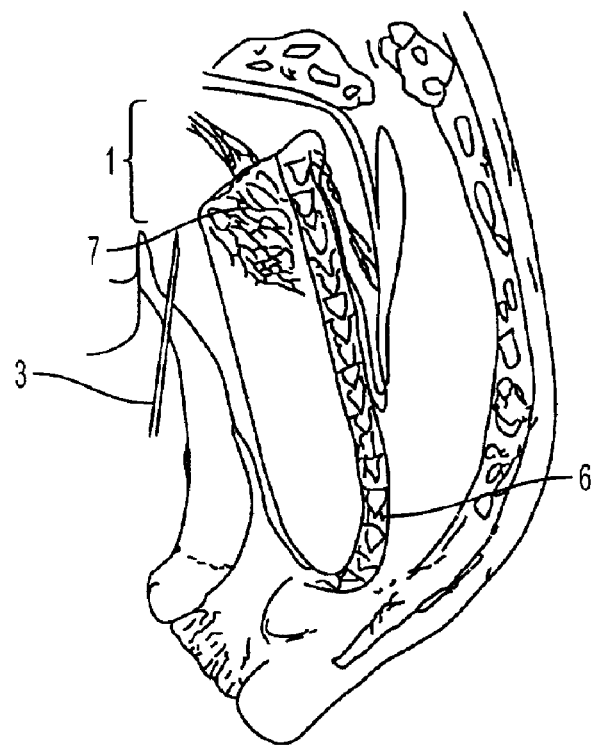
FIG. 2 shows the anterior cephalic region of *Megathura crenulata* in sagittal section showing the location of the buccal sinus 1, radula 6, radular muscles 7, and the hollow needle identifying the point of insertion for collection of hemolymph 3.
Figures 3, 4:
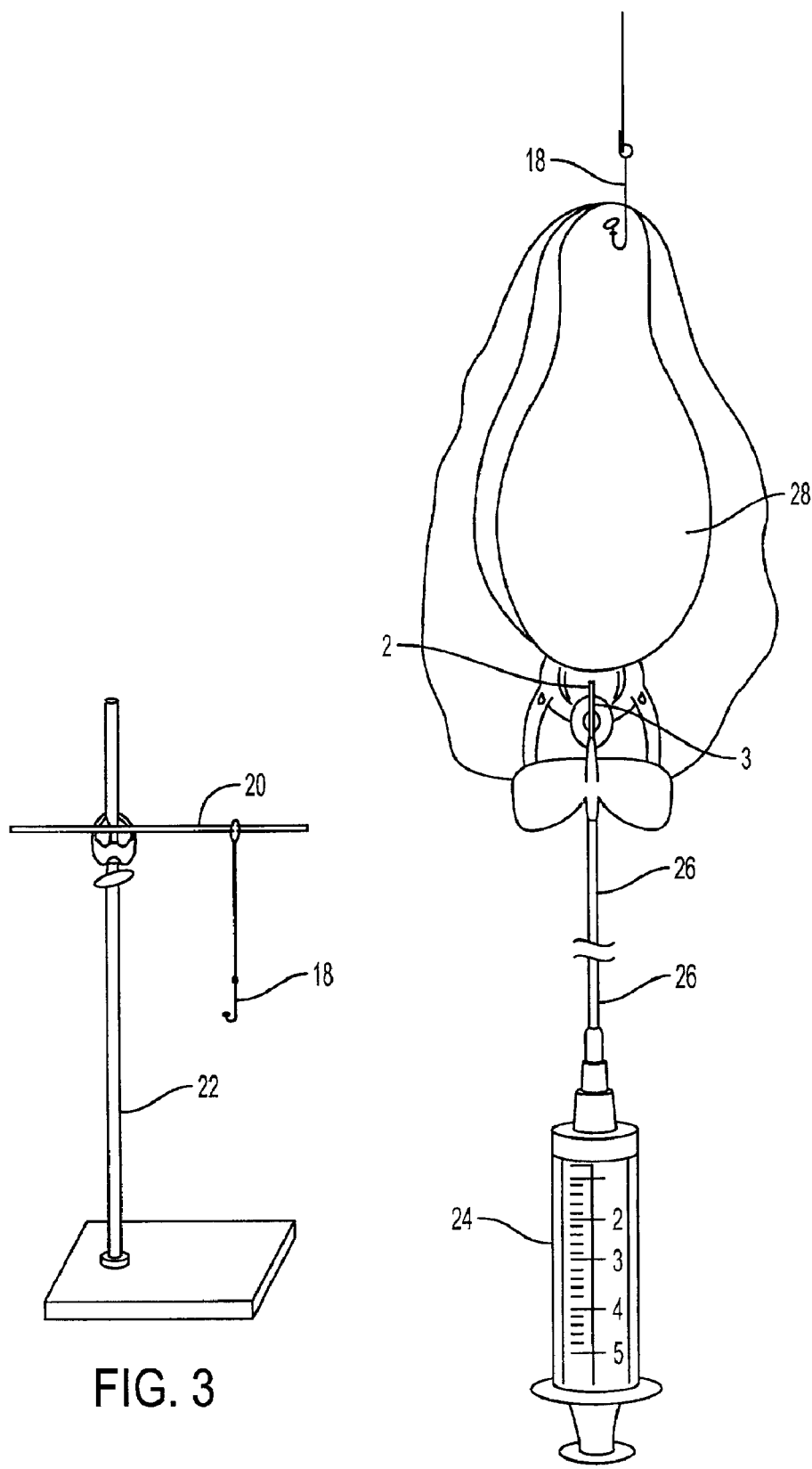
FIG. 3 shows an exemplary apparatus for immobilizing a mollusc according to the method of the invention. A vertical support 20, a horizontal bar 22, and a sterile hook 18 are shown.
FIG. 4 shows a mollusc suspended from an apparatus in a position facilitating insertion of the needle into the buccal sinus for collection of hemolymph. The preferred point of insertion 2 of a hollow needle 3, which is attached to a catheter tube 26 and a collection vessel 24 are shown. The mollusc is suspended from a sterile hook 18 attached to the muscular foot 28 of the animal

In one embodiment of the invention, the apparatus for suspending the mollusc is a sterile hook 18 inserted in the extreme caudal region of the foot of the mollusc and suspended from a horizontal bar (FIG. 3), causing the mollusc to hang in a head-down position (FIG. 4). Alternatively, a gripping device can grasp the body or shell of the mollusc and attach to a horizontal or vertical support in such a way as to hold the mollusc in the desired position.

In yet another embodiment of the invention, centrifugation or another suitable method can be used to concentrate hemolymph in a sinus region of the animal and collect in a sinus region, such as the buccal sinus 1 or cardiac blood sinus 8.

Hemolymph can also be concentrated in a sinus region of a mollusc by placing the animal in a receiver, such as a tapered cylinder with an opening at the small end allowing the animal's head to protrude, with the small end pointing in a downward direction causing the hemolymph to collect in the desired location.

Following isolation of hemolymph in a sinus region of the animal, a sub-lethal quantity of hemolymph is extracted from the animal using any suitable means, such as a sterile hollow needle. If desired, a hollow needle can be connected to a sterile collection vessel, syringe, or other container. In one embodiment, the collection of hemolymph according to the invention utilizes a sterile needle 3, sterile catheter tube 26, and a sterile collection vessel 24.

By insertion of a hollow needle 3, which is attached by a catheter tube 26 connected to a collection vessel 24, into the buccal sinus 1, followed by positioning of the collection vessel 24 below the level of the head of the mollusc resulting in a slight negative pressure, hemolymph will flow through the needle into the collection vessel 24. The hemolymph flows through the needle into a collection vessel by the force of gravity or drawn from the sinus through the needle by application of a vacuum.

Collection of hemolymph can be conducted in a class 10,000 clean room environment at a suitable temperature, such as at about 4° C., using good laboratory practices commonly applied by a person skilled in the art. Such a process meets Good Manufacturing Procedures (GMP) required by the U.S. Food and Drug Administration for products to be used in drug compositions.

Care must be taken to ensure that the needle penetrates only the buccal sinus, and does not penetrate the esophagus, radula 6, radular muscles 7, or other anatomical structures proximate the buccal sinus 1. Through the continued application of slight negative pressure or a vacuum over a period of approximately 60 minutes, a commercially significant but sub-lethal quantity of hemolymph can be obtained.

The volume of hemolymph that can safely be extracted without adversely affecting the health of the source animal varies by species. Less than about 40% of the original animal weight by volume, calculated as the volume of hemolymph milliliters divided by the original animal weight in grams, has proven to be a reliable average for the gastropod *Megathura crenulata*. In other embodiments of the invention, less than about 35%, less than about 30%, less than about 25%, less than about 20%, less than about 15%, less than about 10%, less than about 5%, or less than about 1% of the original animal weight by volume, calculated as the volume of hemolymph milliliters divided by the original animal weight in grams, can be extracted without adverse effects upon the source animal.

Following collection, the source animal is returned to a suitable aquatic environment for recovery.

The following example is given to illustrate the present invention. It should be understood, however, that the invention is not to be limited to the specific conditions or details described in the example. Throughout the specification, any and all references to a publicly available document, including a U.S. patent, are specifically incorporated by reference.

Example 1

The purpose of this example was to demonstrate that commercially significant volumes of hemolymph could be repeatedly extracted from the same gastropod mollusc without adversely impacting the health of the animal.

A five month study was conducted in which twenty healthy specimens of the genus *Megathura* (Giant Keyhole Limpet) were divided into four groups of five animals and placed in a controlled-environment aquaculture system. Three of the groups were subjected to hemolymph extraction at periodic intervals (Group 1: 9 week intervals; Group 2: 6 week intervals; and Group 3: 4 week intervals). The fourth group was used as a control.

For extraction, the mollusc was immobilized in a head down position using an apparatus (see e.g. FIG. 4). A hollow needle was inserted into the buccal sinus and the volume of hemolymph that could be extracted in one hour was collected.

The volume of hemolymph, animal weight, hemolymph protein isoform profile, and animal survival data were recorded for each extraction. Animal weight and protein profile data for the control group was recorded monthly. Protein data for the control group was determined from a 300-microliter aliquot of hemolymph, which was collected monthly (i.e., at 4 week intervals) according to the method of the invention.

The survival for all groups during the five-month study was 100%. The data from the animal weight, hemolymph volume, and protein isoform profile studies are presented below in Table 1.

| Hemolymph Extraction Study | | | | | | |
|---|---|---|---|---|---|---|
| Group 1 | Extraction 1 | Extraction 2 | Extraction 3 | Average | | |
| Volume in ml | 107 | 87 | 63 | 85 | | |
| Average Wt in g | 169 | 140 | 142 | 150 | | |
| % vol./wt. | 13% | 12% | 9% | 11% | | |
| % Isoform 1 | 61% | 55% | 58% | 58% | | |
| Group 2 | Extraction 1 | Extraction 2 | Extraction 3 | Extraction 4 | Average | |
| Volume in ml | 101.4 | 157 | 154 | 73.00 | 121 | |
| Average Wt in g | 267 | 238 | 226 | 229 | 240 | |
| % vol./wt. | 8% | 13% | 14% | 6% | 10% | |
| % Isoform 1 | 56% | 61% | 61% | 55% | 58% | |
| Group 3 | Extraction 1 | Extraction 2 | Extraction 3 | Extraction 4 | Extraction 5 | Average |
| Volume in ml | 154 | 70 | 100 | 73 | 85 | 96.08 |
| Average Wt in g | 361 | 269 | 282 | 275 | 276 | 293 |
| % vol./wt. | 9% | 5% | 7% | 5% | 6% | 7% |
| % Isoform 1 | 55% | 74% | 60% | 67% | 56% | 62% |
| Control | Extraction 1 | Extraction 2 | Extraction 3 | Extraction 4 | Extraction 5 | Average |
| Volume in μl | 300 | 300 | 300 | 300 | 300 | |
| Average Wt in g | 188 | 183 | 193 | 196 | 204 | 193 |
| % vol./wt. | NA | NA | NA | NA | NA | NA |
| % Isoform 1 | 65.70% | 55.70% | 58.70% | 60% | 59.70% | 60% |

The results demonstrate that a commercially significant volume of hemolymph can be extracted repeatedly from the same animals without causing adverse impacts or mortality. Specifically, Groups 1, 2, and 3 produced on average 85 ml, 121 ml, and 96.08 ml of hemolymph per extraction. In addition, more frequent extractions did not result in a decreased collection amount in subsequent extractions. Finally, the results show that repeated extractions according to the invention do not alter the protein characteristics, as the percentage of isoform 1 in the control group is consistent with that observed in test Groups 1–3.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

I claim:

1. A method for obtaining hemolymph from a live gastropod mollusc comprising:
    (a) isolating the hemolymph in the vascular system of the mollusc by immobilizing the mollusc such that gravity acts to pool the hemolymph, thereby collecting the hemolymph in a sinus region, and
    (b) extracting a sub-lethal quantity of hemolymph from the animal via a sinus region.

2. The method of claim 1, wherein the sinus region is selected from the group consisting of the buccal sinus and the cardiac blood sinus.

3. The method of claim 1, wherein said isolating comprises immobilizing the mollusc in a head down position.

4. The method of claim 3, wherein said immobilizing comprises utilizing an apparatus.

5. The method of claim 4, wherein said apparatus is a sterile hook for attaching to the soft body parts of said mollusc.

6. The method of claim 4, wherein said apparatus is a gripping device for grasping the shell of said mollusc.

7. The method of claim 4, wherein said apparatus is a gripping device for grasping the body of said mollusc.

8. The method of claim 4, wherein said apparatus is a tapered cylinder.

9. The method of claim 1, wherein said extraction is performed by inserting a hollow needle into the sinus region.

10. The method of claim 9, wherein said hemolymph is collected in a sterile collection vessel.

11. The method of claim 9, wherein said needle is attached to a syringe and/or a catheter.

12. The method of claim 1, wherein said mollusc is of the genus *Megathura*.

13. The method of claim 1, wherein said mollusc is of the genus *Haliotis*.

14. The method of claim 1, wherein said mollusc is of the genus *Concholepus*.

15. The method of claim 1, wherein said mollusc is of the genus *Fissurella*.

16. The method of claim 1, wherein said mollusc is *Megathura Crenulata*.

17. The method of claim 1, wherein said mollusc is *Haliiotis tuberculata*.

18. The method of claim 1, wherein said mollusc is *Concholepus concholepus*.

19. The method of claim 1, wherein the volume of hemolymph collected is about less than about 40% of the original body weight of said mollusc by volume, calculated as the volume of hemolymph milliliters divided by the original body weight of the mollusc in grams.

20. The method of claim 1, wherein the volume of hemolymph collected is about less than about 35% of the original body weight of said mollusc by volume, calculated as the volume of hemolymph milliliters divided by the original body weight in grams.

21. The method of claim 1, wherein the volume of hemolymph collected is about less than about 30% of the original body weight of said mollusc by volume, calculated as the volume of hemolymph milliliters divided by the original body weight of the mollusc in grams.

22. The method of claim 1, wherein the volume of hemolymph collected is about less than about 25% of the original body weight of said mollusc by volume, calculated as the volume of hemolymph milliliters divided by the original body weight of the mollusc in grams.

23. The method of claim 1, wherein the volume of hemolymph collected is about less than about 20% of the original body weight of said mollusc by volume, calculated as the volume of hemolymph milliliters divided by the original body weight of the mollusc in grams.

24. The method of claim 1, wherein the volume of hemolymph collected is about less than about 15% of the original body weight of said mollusc by volume, calculated as the volume of hemolymph milliliters divided by the original body weight of the mollusc in grams.

25. The method of claim 1, wherein the volume of hemolymph collected is about less than about 10% of the original body weight of said mollusc by volume, calculated as the volume of hemolymph milliliters divided by the original body weight of the mollusc in grams.

26. The method of claim 1, wherein the volume of hemolymph collected is about less than about 5% of the original body weight of said mollusc by volume, calculated as the volume of hemolymph milliliters divided by the original body weight of the mollusc in grams.

27. The method of claim 1, wherein the volume of hemolymph collected is about less than about 1% of the original body weight of said mollusc by volume, calculated as the volume of hemolymph milliliters divided by the original body weight of the mollusc in grams.

* * * * *